(12) United States Patent
Tamura et al.

(10) Patent No.: US 6,593,370 B2
(45) Date of Patent: *Jul. 15, 2003

(54) TOPICAL CAPSAICIN PREPARATION

(75) Inventors: Takashi Tamura, Takatsuki (JP); Urao Kawakami, Nabari (JP); Yuichi Teratani, Soraku-gun (JP); Masakazu Yoshimura, Shijonawate (JP); Masahiko Seto, Kyotanabe (JP)

(73) Assignee: Maruishi Pharmaceutical Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 54 days.

(21) Appl. No.: 09/438,978

(22) Filed: Nov. 12, 1999

(65) Prior Publication Data

US 2002/0058048 A1 May 16, 2002

(30) Foreign Application Priority Data

Nov. 13, 1998 (JP) ............................. 10-341125

(51) Int. Cl.[7] .......................... A61K 31/16; A61K 9/68
(52) U.S. Cl. ...................... 514/627; 514/887; 514/817; 424/400
(58) Field of Search .................. 424/400; 514/627, 514/817, 887

(56) References Cited

U.S. PATENT DOCUMENTS

| 4,702,916 A | * | 10/1987 | Geria ............................ 424/400 |
| 4,992,478 A | * | 2/1991 | Geria |
| 5,178,879 A | | 1/1993 | Adekunle et al. |
| 5,318,960 A | | 6/1994 | Toppo |
| 5,747,049 A | * | 5/1998 | Tominaga ........................ 424/401 |
| 5,827,886 A | * | 10/1998 | Hersh ........................... 514/562 |
| 5,849,272 A | * | 12/1998 | Baba et al. |
| 6,174,891 B1 | * | 1/2001 | Nagase et al. ............... 514/282 |

FOREIGN PATENT DOCUMENTS

FR  2760363 A1  9/1998

OTHER PUBLICATIONS

Abstract of French Patent FR 2760363, Sep. 11, 1998.

M. Houtkappe, et al. The Clinical Journal of Pain, 14:97–106, 1998.

A. Peikert, et al. J. Neurol (1991) 238:452–456.

A. Wantenabe et al., Pain Clinic, 5:709–713, 1994, Abstract.

J.E. Bernstein, et al., J.Am. Acad. Dermatol., 21:265–270, 1989.

C.P.N. Watson, et al., Clin. Ther., 15:510–526, 1993.

N. Jancso, et al., Br. Journal. Pharmac. Chemother. (1967), 31:138–151.

* cited by examiner

*Primary Examiner*—Theodore J. Criares
(74) *Attorney, Agent, or Firm*—Millen, White, Zelano & Branigan, P.C.

(57) ABSTRACT

A topical capsaicin preparation for the treatment of painful cutaneous disorders and neural dysfunction is disclosed. The preparation contains a nonionic, amphoteric or cationic surfactant in an amount effective to eliminate or substantially ameliorate burning pain caused by capsaicin.

11 Claims, No Drawings

TOPICAL CAPSAICIN PREPARATION

BACKGROUND OF THE INVENTION

This invention relates to a topical capsaicin preparation. Capsaicin, the primary pungent principle in the fruit of capsicum plants, produces marked alterations in the function of a defined subpopulation of unmyelinated sensory afferents, termed C-polimodal nociceptors. Following the initial period of intense burning or stinging pain accompanied by erythema, topical capsaicin application causes insensitivity to further irritation by a variety of noxious stimuli. Accordingly, topical preparations of capsaicin find use as a topical therapy for a variety of cutaneous disorders that involve pain and itching, such as postherpetic neuralgia, diabetic neuropathy, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis. Martin Hautkappe et al., Review of the Effectiveness of Capsaicin for Painful Cutaneous Disorders and Neural Dysfunction, Clin. J. Pain, 14:97–106, 1998.

Because of intense burning or stinging pain, many patients are not tolerated in the long-term treatment with topical capsaicin and, therefore, have to discontinue the treatment before appearance of analgesic effect of capsaicin through prolonged administration. It was reported that 26 out of 39 (66.7%) patients suffering from postherpetic neuralgia were not tolerated with a 0.025% capsaicin preparation (Zostrix, Gen Derm, USA). With a 0.075% preparation (Zostrix-HP, Gen Derm, USA), 5 out of 16 (31.3 %) and 45 out of 74 (60.8%) patients with postherpetic neuralgia were not tolerated. Peikert, A. et al., Topical 0.025% capsaicin in chronic post-herpetic neuralgia: efficacy,predictors of response and long-term course, J. Neurol. 238:452–456, 1991; Watanabe, A. et al., Efficacy of capsaicin ointment (Zostrix) in the treatment of herpetic pain and postherpetic neuralgia, Pain Clinic 15:709–713, 1994; Bernstein J. E. et al., Topical capsaicin treatment of chronic postherpetic neuralgia, J. Am. Acad. Dermatol. 21: 265–270, 1989; and Watson C. P. N. et al., A randomized vehicle-controlled trial of topical capsaicin in the treatment of postherpetic neuralgia, Clin. Ther. 15:510–526, 1993.

A need exists for a topical capsaicin preparation which eliminates or substantially ameliorates initial stinging pain caused by capsaicin observed in the administration thereby making the preparation tolerable in long-term administration.

SUMMARY OF THE INVENTION

We have found that the initial stinging pain caused by capsaicin is eliminated or substantially ameliorated by incorporating a large excess of nonionic, amphoteric or cationic surfactants into the topical capsaicin preparation.

Accordingly, the present invention provide a topical preparation comprising (a) an amount of capsaicin effective in long-term or repeated administration to cause insensitivity to painful stimuli associated with painful cutaneous disorders and neural dysfunction, and (b) an amount of a nonionic, amphoteric or cationic surfactant effective to eliminate or substantially ameliorate the initial stinging pain caused by capsaicin, in admixture with a pharmaceutically acceptable carrier for topical administration. Preferably, capsaicin is the sole agent acting on the nervous system contained in the preparation.

The term "substantially ameliorate" as used herein refers to at least 50%, preferably at least 70% and most preferably at least 90% of patients can tolerate the long-term administration of capsaicin to cause insensitivity to painful stimuli. The amount of surfactants to achieve the above effect lies in the range between about 5% and about 20% and preferably in the range between about 9% and 18% by weight of the preparation. When combined with the surfactant, the amount of capsaicin in the topical preparation may be increased to at least about 0.1% by weight although 0.075% of capsaicin has been believed to be maximum.

DETAILED DESCRIPTION

As is known, capsaicin acts on C fibers which serve to transmit the pain impulse to the central nervous system. Initial administration of capsaicin stimulates the C fibers to cause intense burning or stinging pain. Continued administration thereof, however, suppresses the inherent function of these sensory nerve fibers to cause insensitivity to painful and other sensory stimuli.

As a preliminary study, we have tested certain surfactants for the effect on the neuropharmacology of capsaicin.

1. 0.1% capsaicin solutions containing varying amount of polyoxyethylene (60) hydrogenated castor oil were prepared by dissolving 0.1 g of capsaicin and 0, 3, 9 or 18 g of the surfactant in 26.4 ml of ethanol and then diluting with distilled water q.s. to make a total volume of 100 ml.

Each of 0.1% capsaicin solution thus prepared was applied to the hind-limb of rats. One hour after the application, the limb was placed in a water bath warmed at 42° C. and the length of time (in seconds) elapsed until when the rat withdrew the treated limb from the water bath was determined. The results are shown in Table 1.

TABLE 1

Withdrawal latency to thermal stimuli of hind-limb in rat during sensitization by capsaicin

| Surfactant concentration (%) | Withdrawal latency time (sec.) | |
| --- | --- | --- |
|  | Before appln. | One hour after appln. |
| 0 | 30 ± 0 | 2.45 ± 0.32 |
| 3 | 30 ± 0 | 20.29 ± 4.18 |
| 9 | 30 ± 0 | 30 ± 0 |
| 18 | 30 ± 0 | 27.28 ± 2.35 |

As shown in Table 1, application of 0.1% capsaicin solution without polyoxyethylene hydrogenated castor oil remarkably shortened the withdrawal latency compared to the withdrawal latency measured before application of the test solution. The withdrawal latency was slightly shortened at a surfactant concentration of 3% but was not affected significantly at a surfactant concentration of 9% and 18%, respectively.

These results demonstrate that the response of sensory nerves to thermal stimuli during sensitization by capsaicin is suppressed by co-administration of polyoxyethylene hydrogenated castor oil at a concentration of 9% or higher.

2. The effect of polyoxyethylene (60) hydrogenated castor oil on the eye-wiping reflex caused by capsaicin and the desensitization to chemical stimuli was studied according to the eye-wiping method reported by Jancso N. et al., in "Direct evidence for neurogenic inflammation and its prevention by denervation and by pretreatment with capsaicin", Br. J. Phamac. Chemother. 31: 138–151, 1967.

When one drop of 0.1% capsaicin solution was applied to the cornea of rats, the animal immediately began to wipe the cornea with front paws and continued the wiping for about 1 minute. The number of this wiping (first wiping) was not virtually affected by the addition of polyoxyethylene hydrogenated castor oil at a concentration of 3%, 9% or 18% to the 0.1% capsaicin solution.

The pretreatment with 0.1% capsaicin solution containing the surfactant at 0%, 3%, 9% or 18% significantly reduced the number of wiping (second wiping) caused by 0.1% capsaicin solution without the surfactant applied 2 hours after the pretreatment. See, Table 2. The pretreatment with the solvent containing the surfactant alone at 0%, 3%, 9% or 18% did not reduce the number of wiping caused by 0.1% capsaicin solution applied 2 hours after the pretreatment. See, Table 3.

TABLE 2

Effect of pretreatment with capsaicin in combination with polyoxyethylene hydrogenated castor oil at various concentrations on the eye-wiping reflex caused by capsaicin.

| Surfactant concentration (%) | Number of wiping | |
|---|---|---|
| | First | Second |
| 0 | 21.5 ± 1.6 | 9.7 ± 1.6 |
| 3 | 24 ± 2.1 | 11.5 ± 0.9 |
| 9 | 23.5 ± 1.1 | 13 ± 0.7 |
| 18 | 22 ± 1.4 | 11.7 ± 0.6 |

TABLE 3

Effect of pretreatment with polyoxyethylene hydrogenated castor oil at various concentrations on the eye-wiping reflex caused by capsaicin.

| Surfactant concentration (%) | Number of wiping | |
|---|---|---|
| | First | Second |
| 0 | 5.2 ± 0.7 | 20.7 ± 1 |
| 3 | 5.3 ± 1 | 21.5 ± 2.2 |
| 9 | 5.8 ± 0.9 | 23.2 ± 0.9 |
| 18 | 4.7 ± 0.9 | 20.5 ± 1 |

The above test results demonstrate that polyoxyethylene-hydrogenated castor oil does not affect the desensitization of sensory nerves caused by capsaicin.

3. The effect of various surfactants on the neural stimuli caused by capsaicin was evaluated by repeating the procedure of Test 1 using test solutions containing capsaicin at 0.1% and a surfactant at 9% or 18%.

The test solutions were prepared by dissolving 0.1 g of capsaicin and 9 g or 18 g of a selected surfactant in 26.4 ml of ethanol and then diluting with distilled water q.s. to make the total volume of 100 ml. The control solution was identical to the test solutions except for the exclusion of the surfactant.

The surfactants used are shown in Table 4 below.

TABLE 4

| Solution No. | Type | Name |
|---|---|---|
| 1 | Nonionic | Polyoxyethylene (60) hydrogenated castor oil; |
| 2 | Nonionic | Polyethylene glycol (45) monostearate; |

TABLE 4-continued

| Solution No. | Type | Name |
|---|---|---|
| 3 | Nonionic | Polyoxyethylene (20) oleyl ether; |
| 4 | Nonionic | Poloxamer 235; |
| 5 | Nonionic | Polyoxyethylene (7.5) nonylphenyl ether; |
| 6 | Nonionic | Polyoxyethylene (60) sorbitol tetraoleate; |
| 7 | Nonionic | Polyoxyethylene (10) castor oil; |
| 8 | Anionic | Sodium polyoxyethylene (2) lauryl ether sulfate; |
| 9 | Amphoteric | N-Dodecyl-N,N-dimethylglycine; |
| 10 | Cationic | Cetyltrimethylammonium chloride. |

As in Test 1, the length of time elapsed until when the rat withdrew the paw from the water bath warmed at 42° C. was determined before and 1 hour after the application of the test solution. At a surfactant concentration of 9%, the withdrawal latency was not virtually shortened one hour after the application of the sample solution while the control solution without surfactant largely shortened the withdrawal latency. See, Table 5. At a surfactant concentration of 18%, all sample solutions except solution No. 8 containing sodium polyoxyethylene (2) lauryl ether sulfate did not shorten the withdrawal latency. See, Table 6.

TABLE 5

Effect of various surfactants at 9% on the withdrawal latency to thermal stimuli of hind-limb in rats during sensitization by capsaicin.

| | Withdrawal latency time (sec.) | |
|---|---|---|
| Sample No. | Before appln. | One hour after appln. |
| Control | 30 ± 0 | 7.35 ± 3.5 |
| 1 | 30 ± 0 | 30 ± 0 |
| 2 | 30 ± 0 | 30 ± 0 |
| 3 | 30 ± 0 | 30 ± 0 |
| 4 | 30 ± 0 | 30 ± 0 |
| 5 | 30 ± 0 | 30 ± 0 |
| 6 | 30 ± 0 | 30 ± 0 |
| 7 | 30 ± 0 | 26.1 ± 2.59 |
| 8 | 30 ± 0 | 28.3 ± 1.71 |
| 9 | 30 ± 0 | 26.74 ± 3.26 |
| 10 | 30 ± 0 | 30 ± 0 |

TABLE 6

Effect of various surfactants at 18% on the withdrawal latency to thermal stimuli of hind-limb in rats during sensitization by capsaicin.

| | Withdrawal latency time (sec.) | |
|---|---|---|
| Sample No. | Before appln. | One hour after appln. |
| Control | 29.34 ± 0.42 | 8.8 ± 4.71 |
| 1 | 29.34 ± 0.43 | 30 ± 0 |
| 2 | 29.34 ± 0.44 | 29.17 ± 0.84 |
| 3 | 29.31 ± 0.47 | 30 ± 0 |
| 4 | 29.32 ± 0.47 | 30 ± 0 |
| 5 | 29.31 ± 0.5 | 30 ± 0 |
| 6 | 29.3 ± 0.52 | 30 ± 0 |
| 7 | 29.35 ± 0.53 | 30 ± 0 |
| 8 | 29.44 ± 0.56 | 19.25 ± 3.72 |
| 9 | 29.43 ± 0.57 | 28.23 ± 1.46 |
| 10 | 29.37 ± 0.64 | 29.31 ± 0.69 |

The above test results demonstrate that the response of sensory nerves to thermal stimuli during sensitization by capsaicin is significantly suppressed by co-administration of various surfactants at a concentration of 9% or higher.

4. The effect of various surfactants on the desensitization of sensory nerves by 0.1% capsaicin was evaluated using the procedure of Test 2.

The sample solution contained capsaicin at 0.1% and a surfactant listed in Table 4 at 18%.

The pretreatment with sample solutions significantly reduced the number of wiping (second wiping) caused by 0.1% capsaicin solution without the surfactant applied one hour after the pretreatment. See, Table 7.

The pretreatment with solutions only containing the surfactants did not affect the number of wiping (second wiping) caused by 0.1% capsaicin solution without the surfactant applied one hour after the pretreatment. See, Table 8.

TABLE 7

Effect of pretreatment with capsaicin in combination with various surfactants on the eye-wiping reflex caused by capsaicin.

| | Number of wiping | |
|---|---|---|
| Sample No. | First | Second |
| Control | 22.2 ± 1.4 | 12 ± 2.8 |
| 1 | 25.3 ± 2.2 | 10.5 ± 2.3 |
| 2 | 23.7 ± 3.8 | 13.3 ± 2.6 |
| 3 | 23.8 ± 2.3 | 10.2 ± 2.9 |
| 4 | 25.5 ± 2.2 | 13.7 ± 2.1 |
| 5 | 27.5 ± 2.5 | 13.5 ± 1.4 |
| 6 | 23.8 ± 1.5 | 16.2 ± 2.1 |
| 7 | 26 ± 3.3 | 13.3 ± 2.7 |
| 8 | 25 ± 2.3 | 15.3 ± 2.7 |
| 9 | 21.7 ± 1.7 | 12.5 ± 1.6 |
| 10 | 23.5 ± 1.3 | 15.3 ± 1 |

TABLE 8

Effect of pretreatment with varius surfactants on the eye-wiping reflex caused by capsaicin.

| | Number of wiping | |
|---|---|---|
| Sample No. | First | Second |
| Control | 5.5 ± 0.6 | 22.5 ± 2 |
| 1 | 4.3 ± 0.5 | 22.7 ± 3.7 |
| 2 | 3 ± 0.6 | 22.8 ± 2.6 |
| 3 | 5.2 ± 0.4 | 21.3 ± 1.4 |
| 4 | 4.3 ± 0.7 | 22.5 ± 1.1 |
| 5 | 5.3 ± 0.6 | 21 ± 1.2 |
| 6 | 3.8 ± 0.9 | 22.7 ± 1 |
| 7 | 3.8 ± 0.6 | 24.7 ± 3.3 |
| 8 | 6.5 ± 0.8 | 24 ± 2.1 |
| 9 | 7 ± 0.9 | 20 ± 1.9 |
| 10 | 6.8 ± 0.8 | 24.5 ± 3.4 |

The above test results demonstrate that the addition of various surfactants to 0.1% capsaicin does not affect the known desensitization of sensory nerves with capsaicin itself.

The topical capsaicin preparation of this invention finds use in the treatment of painful cutaneous disorders and neural dysfunction including but not limited to postherpetic neuralgia, diabetic neuralgia, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis.

The topical capsaicin preparation of this invention may take the form of liquids, ointments, creams, gels, plasters or other forms adapted for topical application. These preparations may be manufactured by the methods well-known in the art and may comprise a mineral oil such as liquid paraffin or vaseline, a fatty alcohol such as cetyl or stearyl alcohol, a gelling agent such as carboxyvinyl polymers or fatty amines, and other conventional additives such as preservatives, perfumes, coloring agents and the like. Capsaicin is hardly soluble in water but easily soluble in oils and ethanol. Because of this, the topical capsaicin preparation preferably comprises a medium in which capsaicin is easily soluble.

A variety of nonionic, amphoteric and cationic surfactants are known and may be used in the present invention. Non-limiting examples of nonionic surfactants included polyoxyethylene castor oil such as polyoxyethylene (10) castor oil; polyoxyethylene hydrogenated castor oil such as polyoxyethylene (60) hydrogenated castor oil; polyethylene glycol fatty acid ester such as polyethylene glycol (45) monostearate; polyoxyethylene alkyl ether such as polyoxyethylene (20) oleyl ether; polyoxyethylene-polyoxypropylene alkyl ether such as poloxamer 235; polyoxyethylene alkylphenyl ether such as polyoxyethylene (7.5) nonylphenyl ether; and polyoxyethylenesorbitol fatty acid ester such as polyoxyethylene (60) sorbitol tetraoleate. Examples of amphoteric surfactants include betaine derivatives such as N-dodecyl-N,N-dimethylglycine betaine. Example of cationic surfactants include cetyltrimethylammonium chloride.

Now the present invention will be described with reference to the following Examples.

EXAMPLE 1

0.1% Cream

| Material | Amount |
|---|---|
| Liquid paraffin | 17 g |
| White vaseline | 5 g |
| Cetyl alcohol | 4 g |
| Polyoxyethylene (60) hydrogenated castor oil | 18 g |
| Triethanolamine | 0.075 g |
| Carbopol 941 | 0.05 g |
| Capsaicin | 0.1 g |
| Sodium edetate | 0.1 g |
| Preservative | q.s. |
| Distilled water | q.s. |
| Total | 100 g |

EXAMPLE 2

0.1% Ointment

| Material | Amount |
|---|---|
| Liquid paraffin | 20 g |
| White vaseline | 52 g |
| Cetyl alcohol | 9.9 g |
| Polyoxyetylene (60) hydrogenated castor oil | 18 g |
| Capsaicin | 0.1 g |
| Total | 100 g |

EXAMPLE 3

0.1% Gel

| Material | Amount |
| --- | --- |
| Polyoxyethylene (60) hydrogenated castor oil | 18 g |
| Carbopol 941 | 0.5 g |
| Ethanol | 22 g |
| Triethanolamine | 1.5 g |
| Capsaicin | 0.1 g |
| Distilled water | 57.9 g |
| Total | 100 g |

EXAMPLE 4

Topical cream preparations containing capsaicin at 0.05% and 0.1%, respectively were produced as in Example 1.

These preparations were tested clinically for the pain relieving efficacy in 15 patients with postherpetic neuralgia.

The patients received the capsaicin cream 3 times daily for consecutive 4 weeks. No patient withdrew from the treatment during this because of intense burning or stinging pain caused by capsaicin. The pain relieving effect was recognized in terms of VAS values at the end of the treatment in 4 out of 6 patients (66.7%) treated with 0.05% capsaicin cream and in 5 out of 9 patients (55.6%) treated with 0.1% capsaicin ream. These results demonstrate that the topical capsaicin preparation of this invention is excellent in efficacy and drug tolerance. It is noteworthy that the concentration of capsaicin may increase up to about 0.1% according to this invention. Heretofore, it is believed that 0.075% of capsaicin is practically maximum in view of intense burning or stinging pain on initial administration.

What is claimed is:

1. A method of relieving pain or itching in a patient having a cutaneous disorder or neural dysfunction that involves pain or itching comprising:

applying to a painful or pruritic site of the skin of said patient a topical composition comprising, in admixture with a pharmaceutically acceptable carrier for topical application, an amount of about 0.025 % to about 2 % by weight, based on the total weight of the topical composition, of capsaicin wherein capsaicin is essentially the sole active agent which acts on the nervous system, and an amount of about 9 % to about 20 % by weight, based on the total weight of the topical composition, of a nonionic, amphoteric or cationic surfactant, effective to eliminate or substantially ameliorate the initial burning and/or stinging pain otherwise induced by capsaicin, wherein the surfactant is a polyoxyethylene castor oil, a polyoxyethylene hydrogenated castor oil, a polyethylene glycol fatty acid ester, a polyoxyethylene alkyl ether, a polyoxyethylene-polyoxypropylene alkyl ether, a polyoxyethylene alkylphenyl ether, a polyoxyethylenesorbitol fatty acid ester, a betaine derivative, cetyltrimethylammonium, chloride or any mixture thereof.

2. The method according to claim 1, wherein said cutaneous disorder or neural dysfunction is postherpetic neuralgia, diabetic neuralgia, pruritus, psoriasis, postmastectomy pain syndrome, cutaneous allergy, neck pain, amputation stump pain, reflex sympathetic dystrophy or pain due to skin tumor.

3. The method to claim 1, wherein said cutaneous disorder or neural dysfunction is postherpetic neuralgia.

4. The method of claim 1, further comprising the step of repeating the application of said topical composition until the sensory nerves in said painful or pruritic site have been desensitized to painful or pruritic stimuli.

5. The method according to claim 1, wherein the surfactant is a polyoxyethylene hydrogenated castor oil.

6. The method of claim 1, wherein the amount of capsaicin is from about 0.075% to 2% by weight, based on the total weight of the topical composition.

7. The method of claim 1, wherein the amount of capsaicin is from more than 0.075% to about 2% by weight, based on the total weight of the topical composition.

8. The method of claim 1, wherein the amount of capsaicin is from about 0.1% to 2% by weight, based on the total weight of the topical composition.

9. The method of claim 1, wherein the surfactant is a non-ionic surfactant which is a polyoxyethylene castor oil, a polyoxyethylene hydrogenated castor oil, a polyethylene glycol fatty acid ester, a polyoxyethylene alkyl ether, a polyoxyethylene-polyethylene alkyl ether, a polyoxyethylene alkylphenyl ether or a polyoxyethylenesorbitol fatty acid ester.

10. The method of claim 1, wherein the surfactant is a betaine derivative.

11. The method of claim 1, wherein the surfactant is cetyltrimethylammonium chloride.

* * * * *